United States Patent [19]

Crossley

[11] 4,337,259
[45] Jun. 29, 1982

[54] PYRIDINE DERIVATIVES

[75] Inventor: Roger Crossley, Reading, England

[73] Assignee: John Wyeth & Brother Limited, Maidenhead, England

[21] Appl. No.: 232,451

[22] Filed: Feb. 9, 1981

[30] Foreign Application Priority Data

Feb. 20, 1980 [GB] United Kingdom ................ 8005668
Feb. 20, 1980 [GB] United Kingdom ................ 8005669

[51] Int. Cl.³ .................... C07D 213/32; A61K 31/44
[52] U.S. Cl. ..................................... 424/263; 546/339
[58] Field of Search ................. 546/339, 301; 424/263

[56] References Cited

FOREIGN PATENT DOCUMENTS 45-24599 8/1970 Japan .................................. 546/339

OTHER PUBLICATIONS

Bauer et al., Journal of Organic Chemistry, vol. 28, pp. 1323–1328, (1963).

Primary Examiner—Alan L. Rotman
Attorney, Agent, or Firm—George Tarnowski

[57] ABSTRACT

The invention relates to a pharmaceutical composition comprising an anti-ulcer effective amount of a compound of formula I

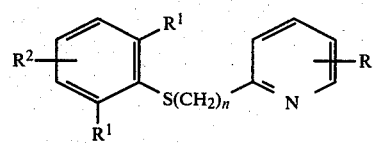

wherein R represents hydrogen, lower alkyl, phenyl, halophenyl, loweralkylphenyl, loweralkoxyphenyl, or aralkyl of 7 to 12 carbon atoms, $R^1$ represents hydrogen or lower alkoxy, $R^2$ represents hydrogen, chlorine or trifluoromethyl and n is 1 or 2, or a pharmaceutically acceptable acid addition salt thereof, and a pharmaceutically acceptable carrier.

A method of treating ulcers or hypersecretion in a mammal which comprises administering a compound of formula I is also disclosed. Some compounds of formula I are novel and within the scope of the invention.

9 Claims, No Drawings

PYRIDINE DERIVATIVES

The invention relates to pyridine derivatives which show activity in tests for anti-ulcer and/or anti-secretory activity.

In a search for novel anti-ulcer agents I have found that certain 2-(arylthiomethyl) pyridine derivatives possess activity in tests for anti-ulcer or anti-secretory activity and hence are of value in the treatment of ulcers or hypersecretion in mammals. Some of these compounds are known chemicals others are novel.

Accordingly in one aspect the invention provides a pharmaceutical composition comprising an anti-ulcer effective amount of a compound of formula I

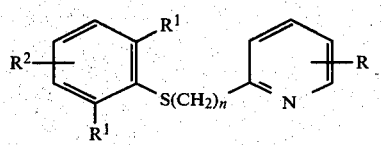

wherein R represents hydrogen, lower alkyl, phenyl, halophenyl, loweralkylphenyl, loweralkoxyphenyl, or aralkyl of 7 to 12 carbon atoms, $R^1$ represents hydrogen or lower alkoxy, $R^2$ represents hydrogen, chlorine or trifluoromethyl and n is 1 or 2, or a pharmaceutically acceptable acid addition salt thereof, and a pharmaceutically acceptable carrier.

In this specification a lower alkyl group has from 1 to 6 carbon atoms e.g. methyl, ethyl, n-propyl, isopropyl, n-butyl, s-butyl, t-butyl, n-pentyl and n-hexyl. A loweralkoxy substituent is alkoxy in which the alkyl portion is as defined for a lower alkyl group. Whenever the term lower alkyl is used as part of another radical, e.g. aryl-loweralkyl, the lower alkyl or lower alkoxy portion has 1 to 6 carbon atoms unless otherwise stated.

The aryl group R is preferably phenyl or substituted phenyl, substituents being halogen, lower alkyl, lower alkoxy and so on. Aralkyl is preferably phenyl lower alkyl.

The acid addition salts of compounds of formula I may be of an organic or inorganic acid, e.g. hydrochloric, hydrobromic, phosphoric, sulphuric, nitric, citric, acetic, formic, fumaric, maleic, tartaric, embonic, methane sulphonic and p-toluene sulphonic acids.

For the pharmaceutical compositions any suitable carrier known in the art can be used. In such a composition, the carrier may be a solid, liquid, or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl callulose, a low melting wax and cocoa butter. The term "composition" is intended to include the formulation of an active ingredient with encapsulating material as carrier, to give a capsule in which the active ingredient (with or without other carriers) is surrounded by carriers which is thus in association with it. Similarly cachets are included.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 10 to 500 mg or more, e.g. 25 mg to 250 mg, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

Anti-ulcer activity was determined by the stress-induced erosion test of Senay and Levine, Proc Soc Exp Biol Med, 124, 1221–3(1967) and anti-secretory activity by the test of H. Shay, D. Sun and H. Gruenstein, Gastroenterology, 1954, 26, 903–13 as exemplified by Beattie et al. J. Med. Chem. 20, 714 (1977). Compounds which possess one or both these activites are considered to be anti-ulcer agents which can be used for the treatment of ulcers or hypersecretion in mammals. The compounds of formula I which we have tested possess one or both of the above activities.

Some compounds of the invention are novel and the invention also concerns novel compounds of formula II

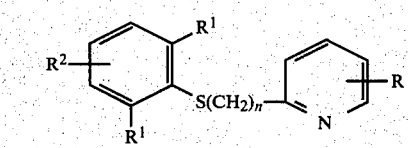

wherein R, $R^1$, $R^2$ and n are defined in connection with formula I but at least one of R, $R^1$ and $R^2$ is other than hydrogen, preferably R is hydrogen.

A compound of formula I wherein R, $R^1$ and $R^2$ are hydrogen and n is 1 is described in J. Org. Chem., 1963, 28, 1323.

The invention includes a method of preparing a novel compound of formula II, which method comprises reacting a thiol compound of formula III, or an alkali metal salt thereof

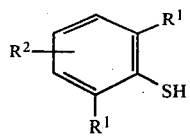

where $R^1$ and $R^2$ are as defined in connection with formula II with a pyridine derivative of formula IV

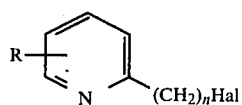

wherein n is 1 or 2, R is as defined in connection with formula II and Hal is a halogen atom, especially chlorine, bromine or iodine.

The invention includes a method of treating ulcers or hypersecretion in a mammal, which method comprises administering to said mammal an effective amount of a compound of formula I or an acid addition salt thereof. The amount of compound used will depend on the activity of the compound and the needs of the mammal being treated. Doses may range from 1 to 100 mg/kg.

The invention is illustrated by the following Examples:

EXAMPLE 1

2-((Phenylthio)methyl)pyridine

Thiophenol (21 ml) was added to a solution of sodium (4.6 g) in ethanol (100 ml). To the resulting solution was added 2-picolyl chloride, hydrochloride (15 g) and the mixture was heated at reflux for 2 hours. Precipitated sodium chloride was removed by filtration and the solution was acidified with ethereal HCl. The solvent was removed by evaporation and the residue induced to crystallise by trituration with ether. Recrystallisation from ethanol-ether gave 2-((phenylthio)methyl)pyridine, hydrochloride (5.0 g) mp 142°–4° C. (Found: C, 60.6; H, 5.25; N, 5.5. $C_{12}H_{11}NS$, HCl requires C, 60.6; H, 5.1; N, 5.9%).

This compound is also described in J. Org. Chem. 1963, 28, 1323.

EXAMPLE 2

2-(((4-Chlorophenyl)thio)methyl)pyridine

4-Chlorobenzenethiol (5 g) in warm ethanol (5 ml) was added to a solution of sodium hydroxide (2.8 g) in ethanol (50 ml). To the solution was added a solution of 2-picolyl chloride, hydrochloride (5.7 g) in ethanol (25 ml) and the mixture was stirred at ambient temperature for 6 hours. The mixture was filtered and evaporated and the residue was converted into the hydrochloride with ethereal HCl solution and this was recrystallised from ethanol-ether to give 2-(((4-chlorophenyl)thio)methyl)pyridine, hydrochloride (8 g) mp 196°–8° C. (Found: C, 52.95; H, 4.1; N, 5.15. $C_{12}H_{10}ClNS$.HCl requires C, 53.1; H, 4.2; N, 4.9%).

EXAMPLE 3

2-(((3-Trifluoromethylphenyl)thio)methyl)pyridine m-Trifluoromethylbenzenethiol (5 g) was added to a solution of NaOH (2.25 g) in ethanol (50 ml) and the resulting solution was treated with a solution of 2-picolyl chloride, hydrochloride (4.6 g) in ethanol (25 ml) and the mixture was stirred for 5 hours. The resulting suspension was filtered through kieselghur and the solvent was removed by evaporation. The residue was converted into the hydrochloride in ether with ethereal HCl and recrystallised from acetone-ether to give 2-(((3-trifluoromethylphenyl)thio)methyl)pyridine hydrochloride (4.8 g) mp 145°–6° C. Found: C, 51.1; H, 4.0; N, 4.7. $C_{13}H_{10}F_3NS$.HCl requires C, 51.0; H, 3.6; N, 4.6%).

EXAMPLE 4

2-(((2-Methoxyphenyl)thio)methyl)pyridine

2-Methoxybenzenethiol (5 g) was added to a solution of sodium hydroxide (2.85 g) in ethanol (50 ml) and the resulting mixture was treated with 2-picolyl chloride, hydrochloride (5.7 g) in ethanol (25 ml) at 0° C. After 16 hours at ambient temperature the mixture was filtered through kieselghur and evaporated. The residue was converted into the hydrochloride in ether with ethereal HCl solution and this was recrystallised from propan-2-ol/acetone to give 2-(((2-methoxyphenyl)thio)methyl)-pyridine, hydrochloride (4.0 g) mp 141°–3° C. (Found: C, 58.5; H, 5.4; N, 4.9. $C_{13}H_{13}NOS$.HCl requires C, 58.3; H, 5.3; N, 5.2%).

EXAMPLE 5

2-Methyl-6-((phenylthio)methyl)pyridine

Following the method of Example 1 thiophenol is reacted with 6-methyl-2-picolyl chloride hydrochloride in the presence of sodium ethoxide to give the title compound.

Pharmaceutical Compositions

The following examples illustrate the preparation of unit dosage form of pharmaceutical compositions according to the invention

EXAMPLE A

| Antacid Tablet (chewable) | |
|---|---|
| Saccharin | 1.0 mg |
| Hydrated alumina sucrose powder | 750.0 mg |
| 2-((Phenylthio)methyl)pyridine | 100.0 mg |
| Mannitol BP | 170.0 mg |
| Maize starch BP dried | 30.0 mg |
| Talc purified BP | 28.0 mg |
| Magnesium stearate BP | 20.0 mg |
| Peppermint oil BP | 1.0 mg |
| | 1100.0 mg |

Antacid tablets of the above formulation are prepared by the following procedure. Triturate peppermint oil with talc (screen 40 mesh). Add the triturate, and other ingredients to a blender and mix thoroughly. Slug the powder to large hard slugs. Granulate the slugs through a 14 mesh screen. Compress the granules on a suitable compression machine to give tablets of the required size.

EXAMPLE B

| Anti-ulcer tablet (without antacid) | mg/tablet |
|---|---|
| 2-((Phenylthio)methyl)pyridine, hydrochloride | 100.0 mg |
| Celutab | 147.5 mg |
| Mg Stearate | 2.5 mg |
| | 150.0 mg |

The tablets are prepared by the following method. Blend the ingredients in a suitable blender. Compress the blended ingredients on a suitable compression machine to form tablets of the above composition. Celutab is a commercial product comprising 90–2% dextrose, 3–5% maltose, the remainder being higher glucose saccharides. The product is spray crystallised.

EXAMPLE C

Example A is repeated but replacing 2-((phenylthio)methyl)pyridine with 100 mg of 2-(((4-chlorophenyl)thio)methyl)pyridine.

EXAMPLE D

Example B is repeated but replacing 2-(((phenylthiomethyl)pyridine)hydrochloride with 100 mg of 2-(((4-chlorophenyl)thio)methyl)pyridine hydrochloride.

| | Pharmacological Test Results | | | |
|---|---|---|---|---|
| | Stress-induced erosion (Senay & Levine) | | Anti-secretory (Shay et al) | |
| Compound [Product of Example No] | Dose mg/kg | % inhibition | Dose mg/kg | % change in vol |
| 1 | 100 | 45 | 30 | −46 |
| 2 | 100 | NS | 30 | −69 |
| 3 | 100 | NS | 30 | −19 |
| 4 | 100 | 56 | 30 | −35 |

NS = not significant

I claim:

1. An anti-ulcer composition comprising an anti-ulcer effective amount of a compound of formula I

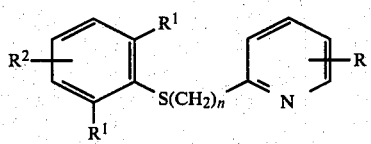

wherein R represents hydrogen or lower alkyl, $R^1$ represents hydrogen or lower alkoxy, $R^2$ represents hydrogen, chlorine or trifluoromethyl and n is 1, or a pharmaceutically acceptable acid addition salt thereof, with the proviso that when $R^2$ is hydrogen or chlorine then at least one of $R^1$ is lower alkoxy, and a pharmaceutically acceptable carrier.

2. An anti-ulcer composition as claimed in claim 1, wherein the compound of formula I is 2-(((trifluoromethylphenyl)thio)methyl)pyridine or a pharmaceutically acceptable acid addition salt thereof.

3. An anti-ulcer composition as claimed in claim 1, wherein the compound of formula I is 2-(((2-methoxyphenyl)thio)methyl)pyridine or a pharmaceutically acceptable acid addition salt thereof.

4. A method of treating ulcers or hypersecretion in a mammal, which method comprises orally administering to said mammal in need of such treatment an effective amount of a compound of formula I

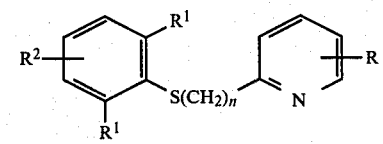

wherein R represents hydrogen or lower alkyl, $R^1$ represents hydrogen or lower alkoxy, $R^2$ represents hydrogen, chlorine or trifluoromethyl and n is 1, or a pharmaceutically acceptable acid addition salt thereof.

5. A method as claimed in claim 4 wherein the compound administered has the formula set forth in claim 4, wherein R is hydrogen.

6. A method as claimed in claim 4 wherein the compound of formula I is a compound selected from the group 2-((phenylthio)methyl)pyridine, 2-(((4-chlorophenyl)thio)methyl)pyridine, 2-(((trifluoromethylphenyl)thio)methyl)pyridine, 2-(((2-methoxyphenyl)thio)methyl)pyridine, or a pharmaceutically acceptable acid addition salt thereof.

7. A compound of formula

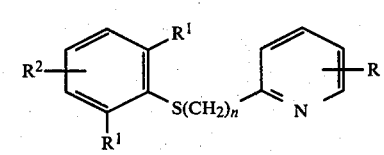

wherein R represents hydrogen or lower alkyl, $R^1$ represents hydrogen, or lower alkoxy, $R^2$ represents hydrogen, chlorine or trifluoromethyl and n is 1, or a pharmaceutically acceptable acid addition salt thereof, with the proviso that when $R^2$ is hydrogen or chlorine then at least one of $R^1$ is lower alkoxy.

8. 2-(((3-Trifluoromethylphenyl)thio)methyl)pyridine or a pharmaceutically acceptable acid addition salt thereof.

9. 2-(((2-Methoxyphenyl)thio)methyl)pyridine or a pharmaceutically acceptable acid addition salt thereof.

* * * * *